Nov. 28, 1967 E. S. BOERNER Plant Pat. 2,779
ROSE PLANT
Filed Sept. 12, 1966
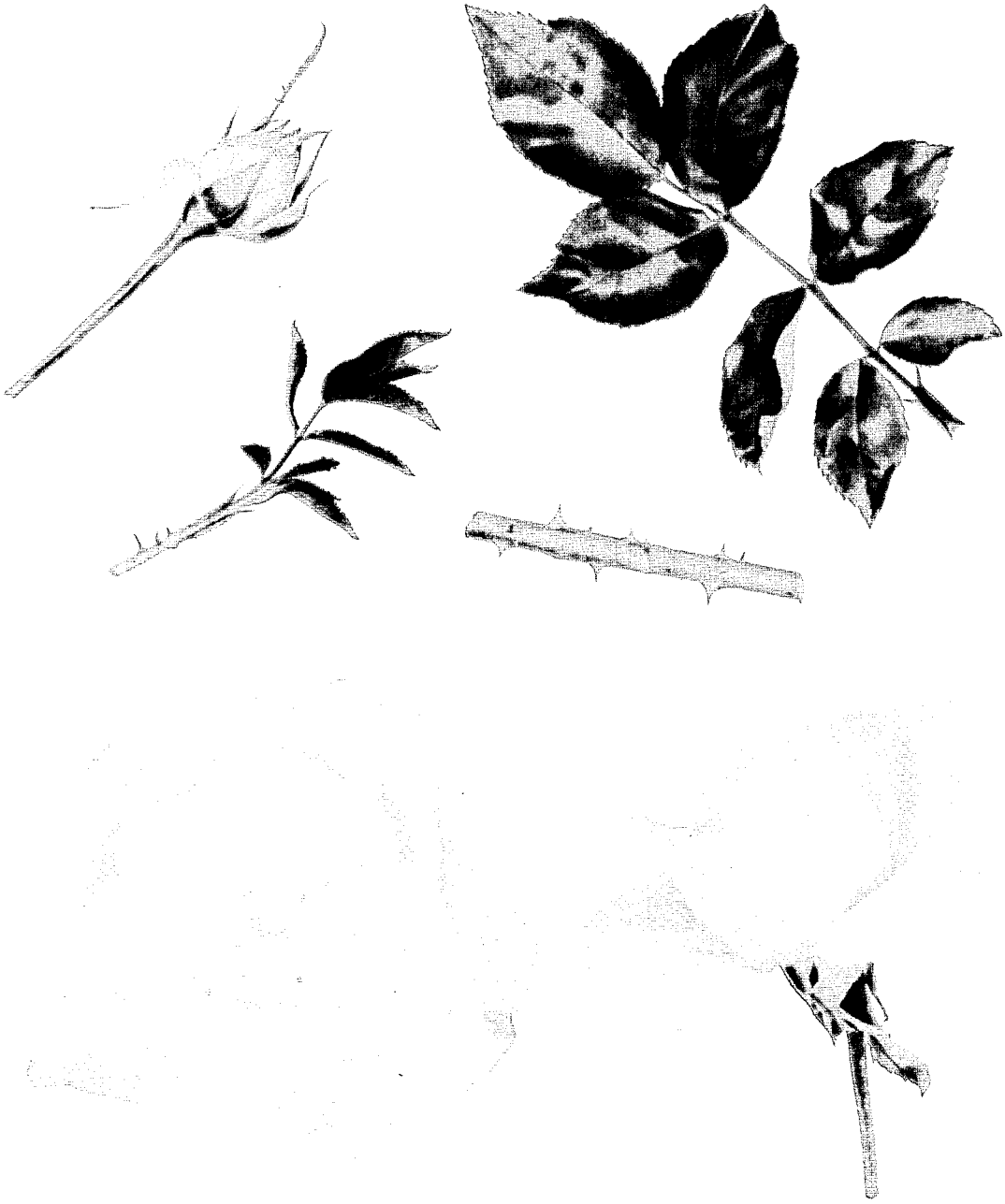
Inventor.
E. S. Boerner
By: Robb & Robb
Attorneys.

United States Patent Office

Plant Pat. 2,779
Patented Nov. 28, 1967

2,779
ROSE PLANT

Eugene S. Boerner, Newark, N.Y., assignor to Jackson & Perkins Company, Newark, N.Y., a corporation of New York Filed Sept. 12, 1966, Ser. No. 578,896
1 Claim. (Cl. Plt.—11)

The present invention relates to a new and distinct variety of rose plant of the hybrid tea class, which was originated by me by crossing an unnamed and unpatented seedling of "Diamond Jubilee" (Plant Patent No. 824) with an unnamed and unpatented seedling of "Fashion" (Plant Patent No. 789).

The primary objective of this breeding was to produce a free flowering hybrid tea rose variety which bears flowers of a color different from the flower colors of the parent varieties. This objective was fully achieved, along with other desirable improvements, as evidenced by the following unique combination of characteristics which are outstanding in the new variety and which distinguish it from its parents, as well as from all other varieties of which I am aware:

(1) A leathery foliage texture;
(2) A free flowering habit;
(3) A high-centered flower form which is retained to the end;
(4) A distinctive and attractive general color tonality of the flowers corresponding to Shrimp Pink, very lightly overcast with Eosine Pink, and with the lower half of the petals being overcast with Lemon Chrome; and
(5) A fruity flower fragrance.

Asexual reproduction of my new variety by budding, as performed at Newark, N.Y., and also at Pleasanton, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Diamond Jubilee."
*Pollen parent.*—An unnamed seedling of "Fashion."
Classification:
*Botanic.*—Hybrid tea.
*Commercial.*—Hybrid tea.

*Flower*

(Observations made from specimens grown outdoors at Newark, N.Y., in the early morning during the latter part of the month of August.)

Blooming habit: Recurrent—continuous.
Bud:
*Size.*—Large.
*Form.*—Ovoid—pointed; is not affected by wet or hot weather.
*Color.*—When sepals first divide—Oxblood Red, Plate 1. When petals begin to unfurl—Carmine, Plate 1, very lightly overcast with Spectrum Red, Plate 1 on the outer edge of the petals. When half-blown—Inside of petals—Scarlet Red, Plate 1, with the lower half of the petals overcast with Wax Yellow, Plate 16. Reverse of petals—Massicot Yellow, Plate 16, with the outer edge of the petals lightly overcast with Spectrum Red, Plate 1.

*Sepals.*—Branched; curl back when petals begin to unfurl. Color—Inside: Absinthe Green, Plate 31. Outside: Varley's Green, Plate 18.
*Calyx.*—Color—Varley's Green, Plate 18. Shape—funnel. Size—small. Aspect—smooth. Odor when rubbed—none.
*Peduncle.*—Length — medium. Aspect — smooth. Strength — erect; heavy. Color — Acajou Red, Plate 13.
*Opening.*—Opens up well; is not affected by adverse weather conditions.

Bloom:
*Size.*—Large. Average size when fully expanded—from 4½ inches to 5 inches.
*Borne.*—Both singly and several together.
*Stems.*—Medium length; strong.
*Form (when first open).*—High-centered. Permanence—retains its form to the end.
*Petalage.*—Double (full but open center). Number of petals under normal conditions—from 35 to 40.
*Color.*—Center of flower—Light Ochraceous—Buff, Plate 15, very lightly overcast with Capucine Orange, Plate 3. Outer petals—Thulite Pink, Plate 26, very lightly overcast with Safrano Pink, Plate 2 in the center of the petals, with the lower half of the petals overcast with Maize Yellow, Plate 4. Base of petals (aiglet)—Lemon Chrome, Plate 4. Inside of petals—Shrimp Pink, Plate 1, very lightly overcast with Eosine Pink, Plate 1, with the lower half of the petals overcast with Lemon Chrome, Plate 4. Reverse of petals—Safrano Pink, Plate 2, with the outer edge of the petals lightly overcast with Thulite Pink, Plate 26. General tonality from a distance—Shrimp Pink, Plate 1, very lightly overcast with Eosine Pink, Plate 1.
*Discoloration.*—General tonality at end of first day—Shrimp Pink, Plate 1, and lightly overcast with Eosine Pink, Plate 1. Second day—Shrimp Pink, Plate 1, and lightly overcast with Eosine Pink, Plate 1. Third day—Shrimp Pink, Plate 1, very lightly overcast with Eosine Pink, Plate 1.

Petals:
*Texture.*—Leathery; is not affected by wet or hot weather.
*Appearance.*—Inside—satiny. Outside—shiny.
*Form.*—Oval; slightly notched.
*Arrangement.*—Imbricated (regularly arranged shingle-like).
*Petaloids in center.*—Few; small.
*Persistence.*—Drop off cleanly.
*Fragrance.*—Strong. Nature—fruity (russet apple).
*Lasting quality.*—On the plant—long. As cut flower—long.

*Genital organs*

Stamens, anthers: Medium size; many; regularly arranged around styles.
*Color.*—Light Cadmium, Plate 4.
Stamens, filaments (threads); Medium length.
*Color.*—Apricot Yellow, Plate 4, with the lower half Begonia Rose, Plate 1.
Pollen: Color—Maize Yellow, Plate 4.
Styles: Bunched; uneven length; medium length; thin.
Stigmas: Color—Marguerite Yellow, Plate 30.
Ovaries: All enclosed in calyx.
Hips: None.
Seeds: None.

*Plant*

Form: Bush.
Growth: Vigorous; upright.
Foliage: Compound of 3–7 leaflets.

*Size.*—Large.

*Quantity.*—Abundant.

*Color.*—New foliage—upper side: Victoria Lake, Plate 1. Under side: Oxblood Red, Plate 1. Old foliage—upper side: Varley's Green, Plate 18. Under side: Rainette Green, Plate 31.

*Shape.*—Oval pointed.

*Texture.* — Upper side—leathery. Under side—smooth.

*Ribs and veins.*—Ordinary.

*Edge.*—Serrated (saw toothed).

*Serration.*—Both double and single; small.

*Leaf stem.*—Color — Yellowish-Citrine, Plate 16. Under side—smooth.

*Stipules.*—Medium length; smooth.

Wood:

*New wood.*—Color — Biscay Green, Plate 17. Bark—smooth.

*Old wood.*—Color — Deep, Dull Yellow-Green, Plate 32. Bark—smooth.

Thorns:

*Thorns.*—Quantity — on main stalks from base: ordinary; on laterals from stalk: ordinary. Form—narrow base; medium length; some hooked downward and some hooked upward. Color (when young)—Carmine, Plate 1. Position—irregular.

*Prickles.*—Quantity—on main stalks: none; on laterals: none.

*Short needles.*—Quantity—on main stalks: none; on laterals: none.

I claim:

A new and distinct variety of rose plant of the hybrid tea class, substantially as herein shown and described, characterized particularly as to novelty by the unique combination of a leathery foliage texture, a free flowering habit, a high-centered flower form which is retained to the end, a distinctive and attractive general color tonality of the flowers corresponding to Shrimp Pink, very lightly overcast with Eosine Pink, and with the lower half of the petals being overcast with Lemon Chrome, and a fruity flower fragrance.

No references cited.

ROBERT E. BAGWILL, *Primary Examiner.*